US006281305B1

(12) United States Patent
Luo

(10) Patent No.: US 6,281,305 B1
(45) Date of Patent: *Aug. 28, 2001

(54) IRON-BASED CATALYST FOR PRODUCING OLIGOMERS OF CONJUGATED DIENES

(75) Inventor: Steven Luo, Akron, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,627

(22) Filed: Nov. 5, 1999

(51) Int. Cl.$^7$ .............................. C08F 4/52; C08F 4/60; C08F 36/04; B01J 31/14

(52) U.S. Cl. ..................... 526/139; 502/152; 502/153; 502/154; 502/155; 502/162; 502/171; 526/136; 526/160; 526/171; 526/335

(58) Field of Search .................... 502/152, 153, 502/154, 155, 162, 171; 526/139, 335, 136, 160, 171

(56) References Cited

U.S. PATENT DOCUMENTS

| | | |
|---|---|---|
| 3,419,505 | 12/1968 | Marsico . |
| 3,457,186 | 7/1969 | Marsico . |
| 3,498,963 | 3/1970 | Ichikawa et al. . |
| 3,725,373 | 4/1973 | Yoo . |
| 3,778,424 | 12/1973 | Sugiura et al. . |
| 3,957,894 | 5/1976 | Saeki et al. . |
| 4,048,418 | 9/1977 | Throckmorton ............... 526/138 |
| 4,168,357 | 9/1979 | Throckmorton et al. ........ 526/139 |
| 4,168,374 | 9/1979 | Throckmorton et al. ........ 526/139 |
| 4,182,813 | 1/1980 | Makino et al. ................ 526/92 |
| 4,379,889 | 4/1983 | Ashitaka et al. .............. 525/247 |
| 4,751,275 | 6/1988 | Witte et al. .................. 526/139 |
| 5,239,023 | 8/1993 | Hsu et al. .................... 526/141 |
| 5,283,294 | 2/1994 | Hsu et al. .................... 525/247 |
| 5,359,997 | 11/1994 | Massie, II et al. ............ 525/237 |
| 5,677,405 | 10/1997 | Goodall et al. ............... 526/281 |
| 5,891,963 | 4/1999 | Brookhart et al. ............. 525/326.1 |
| 5,919,875 | 7/1999 | Luo et al. .................... 526/139 |

OTHER PUBLICATIONS

*Journal of Organic Chemistry*, vol. 30, p. 1661, 1965 no month.
*Bulletin of Chemical Society of Japan*, vol. 38, p. 1243, 1965 no month.
*Bulletin of Chemical Society of Japan*, vol. 39, p. 1357, 1966 no month.
*Chemical Reviews*, R. Baker, vol. 73, p. 598, 1973 no month.
Abstract of Japanese Patent No. 45011154, Oct. 1965.
Syndiotactic 1,2–Polybutadiene with Co–CS$_2$ Catalyst System I. Preparation Properties and Application of Highly Crystalline Syndiotactic 1,2–Polybutadiene, II. Catalyst for Stereospecific Polymerization of Butadiene to Syndiotactic 1,2–Polybutadiene, III. $^1$H and $^{13}$C–NMR Study of Highly Syndiotactic 1,2–Polybutadiene and IV Mechanism of Syndiotactic Polymerization of Butadiene with Cobalt Compounds–Organoaluminum–CS$_2$, *Journal of Polymer Science: Polymer Chemistry Edition*, by H. Ashitaka et al., vol. 21, pp. 1853–1860 and 1951–1995 (1983) no month.

"Conjugated Diene Polymerization," Comprehensive Polymer Science, by Porri and Giarrusso Pergamon Press, Oxford, vol. 4, pp. 53, (1989) no month.

U.S. Patent Application Serial No. 08/996,656, filed on Dec. 23, 1997.

U.S. Patent Application Serial No. 09/173,956, filed on Oct. 14, 1998.

U.S. Patent Application Serial No. 09/172,305, filed on Oct. 14, 1998.

U.S. Patent Application Serial No. 09/172,346, filed on Oct. 14, 1998.

U.S. Patent Application Serial No. 09/328,549, filed on Jun. 9, 1999.

U.S. Patent Application Serial No. 09/088,611, filed on Jun. 1, 1998.

U.S. Patent Application Serial No. 09/434,669, filed on Nov. 5, 1999.

U.S. Patent Application Serial No. 09/475,723, filed on Dec. 30, 1999.

U.S. Patent Application Serial No. 09/475,343, filed on Dec. 30, 1999.

U.S. Patent Application Serial No. 09/475,345, filed on Dec. 30, 1999.

U.S. Patent Application Serial No. 09/475,547, filed on Dec. 30, 1999.

U.S. Patent Application Serial No. 09/439,861, filed on Nov. 12, 1999.

*Primary Examiner*—Elizabeth D. Wood
(74) *Attorney, Agent, or Firm*—David G. Burleson; Arthur M. Reginellli

(57) ABSTRACT

A catalyst composition that is the combination of or the reaction product of ingredients including an iron-containing compound, a hydrogen phosphite, a halogen-containing compound, and an organoaluminum compound. This catalyst composition is particularly useful for preparing oligomers of conjugated dienes.

22 Claims, No Drawings

IRON-BASED CATALYST FOR PRODUCING OLIGOMERS OF CONJUGATED DIENES

FIELD OF THE INVENTION

The present invention generally relates to a catalyst composition for use in oligomerizing conjugated dienes into oligomers. More particularly, the present invention is directed toward an iron-based catalyst composition, and specifically toward one that is formed by combining an iron-containing compound, a hydrogen phosphite, a halogen-containing compound, and an organoaluminum compound.

BACKGROUND OF THE INVENTION

Conjugated dienes such as 1,3-butadiene and isoprene undergo a variety of catalytic oligomerization reactions to give cyclic or acyclic oligomers. These oligomers are valuable feedstocks in the industrial production of fine organic chemicals. For example, the dimers and trimers are utilized as intermediates for synthesizing flame retardants, terpenoid and sesquiterpenoid compounds of biological interest, and fragrances.

Various coordination catalyst systems based on nickel, palladium, cobalt, titanium, chromium, and iron have been reported in the prior art for catalyzing the oligomerization of conjugated dienes (see, e.g., R. Baker, in *Chemical Reviews* 1973, Volume 73, Page 487). The majority of these catalyst systems, however, have no practical utility because they have low activity and poor selectivity. The resulting oligomerization product is often a complicated mixture of cyclic and acyclic dimers, trimers, tetramers, and higher oligomers. Furthermore, some oligomerization catalyst systems also generate a certain amount of polymer in the oligomerization product mixtures.

Several iron-based coordination catalyst systems are known in the prior art for the oligomerization of conjugated dienes. The *Bulletin of Chemical Society of Japan* 1965, Volume 38, Page 1243 discloses a process for the oligomerization of 1,3-butadiene by using a catalyst system comprising iron(III) acetylacetonate and triethylaluminum. The *Bulletin of Chemical Society of Japan* 1966, Volume 39, Page 1357 discloses a process for the oligomerization of 1,3-butadiene by using a catalyst system comprising iron(III) acetylacetonate, triethylaluminum, and triphenylphosphine. And, the *Journal of Organic Chemistry* 1965, Volume 30, Page 1661 discloses a process for oligomerizing 1,3-butadiene in the presence of a catalyst system comprising iron(III) chloride, triphenylphosphine, and triethylaluminum. All of these iron-based catalyst systems, however, have very low activity and poor selectivity, and the resulting oligomerization product is a mixture of cyclic and acyclic dimers, trimers, and higher oligomers, as well as polymer. Therefore, these iron-based catalyst systems have no industrial utility.

Because the oligomers of conjugated dienes are useful and the catalyst systems known heretofore in the art have many shortcomings, it would be advantageous to develop a new and significantly improved catalyst system that has high activity and selectivity for oligomerizing conjugated dienes into oligomers.

SUMMARY OF THE INVENTION

In general the present invention provides a catalyst composition that is the combination of or the reaction product of ingredients comprising an iron-containing compound, a hydrogen phosphite, a halogen-containing compound, and an organoaluminum compound.

The present invention also provides a catalyst composition formed by a process comprising the step of combining an iron-containing compound, a hydrogen phosphite, a halogen-containing compound, and an organoaluminum compound.

The present invention also includes a process for forming conjugated diene oligomers comprising the step of oligomerizing conjugated diene monomers in the presence of a catalytically effective amount of a catalyst composition formed by combining an iron-containing compound, a hydrogen phosphite, a halogen-containing compound, and an organoaluminum compound.

Advantageously, the catalyst composition of the present invention has very high activity, which allows conjugated diene oligomers to be produced in very high yields with low catalyst levels after relatively short oligomerization times. In addition, since the catalyst composition of this invention is highly active, even at low temperatures, the oligomerization of conjugated dienes may be carried out under very mild temperature conditions, thereby avoiding thermal polymerization and/or cracking or other deleterious effects on the oligomerization product. Further, the catalyst composition of the present invention is iron-based, and iron compounds are generally stable, non-toxic, inexpensive and readily available. Furthermore, the catalyst composition of the present invention is very selective. For instance, by utilizing the catalyst composition and the process of the present invention, 1,3-butadiene can be converted substantially quantitatively to acyclic dimers substantially without the production of any other products.

DETAILED DESCRIPTION OF ILLUSTRATIVE EMBODIMENTS

It has now been found that conjugated dienes can be efficiently oligomerized by using an iron-based catalyst composition. The catalyst composition of this invention is formed by combining (a) an iron-containing compound, (b) a hydrogen phosphite, (c) a halogen-containing compound, and (d) an organoaluminum compound. In addition to the iron-containing compound, the hydrogen phosphite, the halogen-containing compound, and the organoaluminum compound, other organometallic compounds or Lewis bases that are known in the art can be added, if desired.

Various iron-containing compounds or mixtures thereof can be utilized as ingredient (a) of the catalyst composition of this invention. It is generally advantageous to employ iron-containing compounds that are soluble in a hydrocarbon solvent such as aromatic hydrocarbons, aliphatic hydrocarbons, or cycloaliphatic hydrocarbons. Hydrocarbon-insoluble iron-containing compounds, however, can be suspended in the oligomerization medium to form the catalytically active species, and are therefore also useful.

The iron atom in the iron-containing compounds can be in various oxidation states including, but not limited to, the 0, +2, +3, and +4 oxidation states. It is preferable to use divalent iron compounds -also called ferrous compounds— wherein the iron is in the +2 oxidation state, and trivalent iron compounds—also called ferric compounds—wherein the iron is in the +3 oxidation state. Suitable types of iron-containing compounds that can be utilized in the catalyst composition of this invention include, but are not limited to, iron carboxylates, iron carbamates, iron dithiocarbamates, iron xanthates, iron β-diketonates, iron alkoxides or aryloxides, iron halides, iron pseudo-halides, iron oxyhalides, and organoiron compounds.

Some specific examples of suitable iron carboxylates include iron(II) formate, iron(III) formate, iron(II) acetate, iron(III) acetate, iron(II) acrylate, iron (III) acrylate, iron (II) methacrylate, iron(III) methacrylate, iron (II) valerate, iron (III) valerate, iron(II) gluconate, iron(III) gluconate, iron(II) citrate, iron(III) citrate, iron(II) fumarate, iron(III) fumarate, iron(II) lactate, iron(III) lactate, iron(II) maleate, iron(III) maleate, iron(II) oxalate, iron(III) oxalate, iron(II) 2-ethylhexanoate, iron(III) 2-ethylhexanoate, iron(II) neodecanoate, iron(III) neodecanoate, iron(II) naphthenate, iron(III) naphthenate, iron(II) stearate, iron(III) stearate, iron(II) oleate, iron(III) oleate, iron(II) benzoate, iron(III) benzoate, iron(II) picolinate, and iron(III) picolinate.

Some specific examples of suitable iron carbamates include iron(II) dimethylcarbamate, iron(III) dimethylcarbamate, iron(II) dietlylcarbamate, iron(III) diethylcarbamate, iron(II) duisopropylcarbamate, iron(II) diisopropylcarbamate, iron (II) dibutylcarbamate, iron (III) dibutylcarbamate, iron(II) dibenzylcarbamate, and iron (III) dibenzylcarbamate.

Some specific examples of suitable iron dithiocarbamates include iron(II) dimethyldithiocarbamate, iron(III) dimethyldithiocarbamate, iron(II) diethyldithiocarbamate, iron(III) diethyldithiocarbamate, iron(II) diisopropyldithiocarbamate, iron (III) dliisopropyldithiocarbamate, iron(II) dibutyldithiocarbamate, iron(III) dibutyldithiocarbamate, iron(II) dibenzyldithiocarbamate, iron(III) dibenzyldithiocarbamate.

Some specific examples of suitable iron xanthates include iron(II) methylxanthate, iron(III) methylxanthate, iron(II) ethylxanthate, iron(III) ethylxanthate, iron(II) isopropylxanthate, iron(III) isopropylxanlhate, iron(II) butylxanthate, iron(III) butylxanthate, iron(II) benzylxanthate, and iron(III) benzylxanthate.

Some specific examples of suitable iron β-diketonates include iron(II) acetylacetonate, iron(III) ace tylacetonate, iron(II) trifluoroacetylacetonate, iron(III) trifluoroacetylacetonate, iron(II) hexafluoroacetylacetonate, iron(III) hexafluoroacctylacetonate, iron(II) benzoylacetonate, iron(III) benzoylacetonate, iron(II) 2,2,6,6-tetramethyl-3,5-heptanedionate, and iron(III) 2,2,6,6-tetramethyl-3,5-heptanedionate.

Some specific examples of suitable iron alkoxides or aryloxides include iron(II) methoxide, iron(III) methoxide, iron(II) ethoxide, iron(III) ethoxide, iron(II) isopropoxide, iron(III) isopropoxide, iron(II) 2-ethylhexoxide, iron(III) 2-ethylhexoxide, iron(II) phenoxide, iron(III) phenoxide, iron(II) nonylphenoxide, iron(III) nonylphenoxide, iron(II) naphthoxide, and iron(III) naphthoxide.

Some specific examples of suitable iron halides include iron(II) fluoride, iron(III) fluoride, iron(II) chloride, iron(III) chloride, iron(II) bromide, iron(III) bromide, and iron(II) iodide. Some representative examples of suitable iron pseudo-halides include iron(II) cyanide, iron(III) cyanide, iron(II) cyanate, iron(III) cyanate, iron(II) thiocyanate, iron (III) thiocyanate, iron(II) azide, iron(III) azide, and iron(III) ferrocyanide (also called Prussian blue). Some representative examples of suitable iron oxyhalides include iron(III) oxychloride and iron (III) oxybromide.

The term "organoiron compound" refers to any iron compound containing at least one covalent iron-carbon bond. Some specific examples of suitable organoiron compounds include bis(cyclopentadienyl)iron(II) (also called ferrocene), bis(pentamethylcyclopentadienyl)iron(II) (also called decamethylferrocene), bis(pentadienyl) iron(II), bis (2,4-dimethylpentadienyl) iron(II), bis(allyl)dicarbonyl)iron (II), (cyclopentadienyl) (pentadienyl)iron(II), tetra(1-norbornyl)iron(IV), (trimethylenemethane)tricarbonyliron (II), bis(butadiene)carbonyl)iron (0), butadienetricarbonyl) iron(0), and bis(cyclooctatetraene)iron(0).

Useful hydrogen phosphite compounds that can be employed as ingredient (b) of the catalyst composition of this invention are either acyclic hydrogen phosphites, cyclic hydrogen phosphites, or mixtures thereof.

The acyclic hydrogen phosphites may be represented by the following keto-enol tautomeric structures:

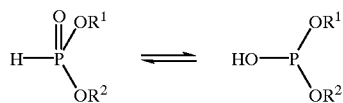

where $R^1$ and $R^2$, which may be the same or different, are mono-valent organic groups. Preferably, $R^1$ and $R^2$ are hydrocarbyl groups such as, but not limited to, alkyl, cycloalkyl, substituted cycloalkyl, alkenyl, cycloalkenyl, substituted cycloalkenyl, aryl, allyl, substituted aryl, aralkyl, alkaryl, and alkynyl groups, with each group preferably containing from 1 carbon atom, or the appropriate minimum number of carbon atoms to form these groups, up to about 20 carbon atoms. These hydrocarbyl groups may contain heteroatoms such as, but not limited to, nitrogen, oxygen, silicon, sulfur, and phosphorus atoms. The acyclic hydrogen phosphites exist mainly as the keto tautomer (shown on the left), with the enol tautomer (shown on the right) being the minor species. The equilibrium constant for the above-mentioned tautomeric equilibrium is dependent upon factors such as the temperature, the types of $R^1$ and $R^2$ groups, the type of solvent, and the like. Both tautomers may be associated in dimeric, trimeric or oligomeric forms by hydrogen bonding. Either of the two tautomers or mixtures thereof can be employed.

Some representative and non-limiting examples of suitable acyclic hydrogen phosphites are dimethyl hydrogen phosphite, diethyl hydrogen phosphite, dibutyl hydrogen phosphite, dihexyl hydrogen phosphite, dioctyl hydrogen phosphite, didecyl hydrogen phosphite, didodecyl hydrogen phosphite, dioctadecyl hydrogen phosphite, bis(2,2,2-trifluoroethyl)hydrogen phosphite, diisopropyl hydrogen phosphite, bis(3,3-dimethyl-2-butyl)hydrogen phosphite, bis(2,4-dimethyl-3-pentyl)hydrogen phosphite, di-t-butyl hydrogen phosphite, bis(2-ethylhexyl)hydrogen phosphite, dineopentyl hydrogen phosphite, bis(cyclopropylmethyl) hydrogen phosphite, bis(cyclobutylmethyl)hydrogen phosphite, bis(cyclopentylmethyl)hydrogen phosphite, bis (cyclohexylmethyl)hydrogen phosphite, dicyclobutyl hydrogen phosphite, dicyclopentyl hydrogen phosphite, dicyclohexyl hydrogen phosphite, dimethyl hydrogen phosphite, diphenyl hydrogen phosphite, dinaphthyl hydrogen phosphite, dibenzyl hydrogen phosphite, bis(1-naphthylmethyl)hydrogen phosphite, diallyl hydrogen phosphite, dimethallyl hydrogen phosphite, dicrotyl hydrogen phosphite, ethyl butyl hydrogen phosphite, methyl hexyl hydrogen phosphite, methyl neopentyl hydrogen phosphite, methyl phenyl hydrogen phosphite, methyl cyclohexyl hydrogen phosphite, methyl benzyl hydrogen phosphite, and the like. Mixtures of the above dihydrocarbyl hydrogen phosphites may also be utilized.

In general, cyclic hydrogen phosphites contain a divalent organic group that bridges between the two oxygen atoms that are singly-bonded to the phosphorus atom. These cyclic hydrogen phosphites may be represented by the following keto-enol tautomeric structures:

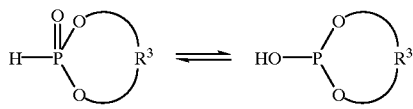

where $R^3$ is a divalent organic group. Preferably, $R^3$ is a hydrocarbylene group such as, but not limited to, alkylene, cycloalkylene, substituted alkylene, substituted cycloalkylene, alkenylene, cycloalkenylene, substituted alkenylene, substituted cycloalkenylene, arylene, and substituted arylene groups, with each group preferably containing from 1 carbon atom, or the appropriate minimum number of carbon atoms to form these groups, up to about 20 carbon atoms. These hydrocarbylene groups may contain heteroatoms such as, but not limited to, oxygen, sulfur, nitrogen, silicon, and phosphorous atoms. The cyclic hydrogen phosphites exist mainly as the keto tautomer (shown on the left), with the enol tautomer (shown on the right) being the minor species. The equilibrium constant for the above-mentioned tautomeric equilibrium is dependent upon factors such as the temperature, the types of $R^3$ group, the type of solvent, and the like. Both tautomers may be associated in dimeric, trimeric or oligomeric forms by hydrogen bonding. Either of the two tautomers or mixtures thereof can be used.

The cyclic hydrogen phosphites may be synthesized by the transesterification reaction of an acyclic dihydrocarbyl hydrogen phosphite (usually dimethyl hydrogen phosphite or diethyl hydrogen phosphite) with an alkylene diol or an arylene diol. Procedures for this transesterification reaction are well known to those skilled in the art. Typically, the transesterification reaction is carried out by heating a mixture of an acyclic dihydrocarbyl hydrogen phosphite and an alkylene diol or an arylene diol. Subsequent distillation of the side-product alcohol (usually methanol or ethanol) that results from the transesteritication reaction leaves the new-made cyclic hydrogen phosphite.

Some specific examples of suitable cyclic alkylene hydrogen phosphites are 2-oxo-(2H)-5-butyl-5-ethyl-1,3,2-dioxaphosphorinane, 2-oxo-(2H)-5,5-dimethyl-1,3,2-dioxaphosphorinane, 2-oxo-(2H)-1,3,2-dioxaphosphorinane, 2-oxo-(2H)-4-methyl-1,3,2-dioxaphosphorinane, 2-oxo-(2H)-5-ethyl-5-methyl-1,3,2-dioxaphosphorinane, 2-oxo-(2H)-5,5-diethyl-1,3,2-dioxaphosphorinane, 2-oxo-(2H)-5-methyl-5-propyl-1,3,2-dioxaphosphorinane, 2-oxo-(2H)-4-isopropyl-5,5-dimethyl-1,3,2-dioxaphosphorinane, 2-oxo-(2H)-4,6-dimethyl-1,3,2-dioxaphosphorinane, 2-oxo-(2H)-4-propyl-5-ethyl-1,3,2-dioxaphosphorinane, 2-oxo-(2H)-4-methyl-1,3,2-dioxaphospholane, 2-oxo-(2H)-4,5-dimethyl-1,3,2-dioxaphospholane, 2-oxo-(2H)-4,4,5,5-tetramethyl-1,3,2-dioxaphospholane, and the like. Mixtures of the above cyclic alkylene hydrogen phosphites may also be utilized.

Some specific examples of suitable cyclic arylene hydrogen phosphites are 2-oxo-(2H)-4,5-benzo-1,3,2-dioxaphospholane, 2-oxo-(2H)-4,5-(3'-methylbenzo)-1,3,2-dioxaphospholane, 2-oxo-(2H)-4,5-(4'-methylbenzo)-1,3,2-dioxaphospholane, 2-oxo-(2H)-4,5 -(4'-tert-butylbenzo)-1,3,2-dioxaphospholane, 2-oxo-(2H)-4,5-naphthalo-1,3,2-dioxaphospholane, and the like. Mixtures of the above cyclic arylene hydrogen phosphites may also be utilized.

The ingredient (c) of the catalyst composition of this invention is a halogen-containing compound that contains one or more halide ions. Some representative examples of these halide ions include, but are not limited to, fluoride, chloride, bromide, and iodide. A combination of two or more of these halide ions can also be utilized. It is generally preferred to employ halogen-containing compounds that are soluble in a hydrocarbon solvent.

Hydrocarbon-insoluble halogen-containing compounds, however, can be suspended in the oligomerization medium to form the catalytically active species, and are therefore also useful.

Suitable types of halogen-containing compounds that can be utilized in the catalyst composition of this invention include, but are not limited to, elemental halogens, mixed halogens, hydrogen halides, organic halides, inorganic halides, metallic halides, and organometallic halides. The preferred halogen-containing compounds are hydrogen halides, metallic halides, and organometallic halides, all of which contain at least one labile halide ion.

Some specific examples of suitable elemental halogens include fluorine, chlorine, bromine, and iodine. Some specific examples of suitable mixed halogens include iodine monochloride, iodine monobromide, iodine trichloride, and iodine pentafluoride.

Some specific examples of suitable hydrogen halides include hydrogen fluoride, hydrogen chloride, hydrogen bromide, and hydrogen iodide.

Some specific examples of suitable organic halides include t-butyl chloride, t-butyl bromides, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzylidene bromide, methyltrichlorosilane, phenyltrichlorosilane, dimethyldichlorosilane, diphenyldichlorosilane, trimethylchlorosilane, benzyl chloride, benzyl bromide, propionyl chloride, propionyl bromide, methyl chloroformate, and methyl bromoformate.

Some specific examples of suitable inorganic halides include phosphorus trichloride, phosphorus tribromide, phosphorus pentachloride, phosphorus oxychloride, phosphorus oxybromide, boron trifluoride, boron trichloride, boron tribromide, silicon tetrafluoride, silicon tetrachloride, silicon tetrabromide, silicon tetraiodide, arsenic trichloride, arsenic tribromide, arsenic triiodide, selenium tetrachloride, selenium tetrabromide, tellurium tetrachloride, tellurium tetrabromide, and tellurium tetraiodide.

Some specific examples of suitable metallic halides include tin tetrachloride, tin tetrabromide, aluminum trichloride, aluminum tribromide, antimony trichloride, antimony pentachloride, antimony tribromide, aluminum trichloride, aluminum tribromide, aluminum triiodide, aluminum trifluoride, gallium trichloride, gallium tribromide, gallium triiodide, gallium trifluoride, indium trichloride, indium tribromide, indium triiodide, indium trifluoride, titanium tetrachloride, titanium tetrafluoride, titanium tetrabromide, titanium tetraiodide, zinc dichloride, zinc dibromide, zinc diiodide, and zinc difluoride.

Some specific examples of suitable organometallic halides include dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, methylmagnesium iodide, ethylmagnesium chloride, ethylmagnesium bromide, butylmagnesium chloride, butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, dibutyltin dichloride, dibutyltin dibromide, tributyltin chloride, and tributyltin bromide.

Various organoaluminum compounds can be utilized as ingredient (d) of the catalyst composition of this invention. As used herein, the term "organoaluminum compound" refers to any aluminum compound containing at least one covalent aluminum-carbon bond. It is generally preferred to employ organoaluminum compounds that are soluble in a hydrocarbon solvent.

A preferred class of organoaluminum compounds that can be utilized is represented by the general formula $AlR_nX_{3-n}$, where each R, which may be the same or different, is a mono-valent organic group, where n is an integer of 1 to 3, and where each X, which may be the same or different, is selected from a hydrogen atom, a halogen atom, a carboxylate group, an alkoxide group, or an aryloxide group. Preferably, each R is a hydrocarbyl group such as, but not limited to, alkyl, cycloalkyl, substituted cycloalkyl, alkenyl, cycloalkenyl, substituted cycloalkenyl, aryl, allyl, substituted aryl, arallkyl, alkaryl, and alkynyl groups, with each group preferably containing from 1 carbon atom, or the appropriate minimum number of carbon atoms to form these groups, up to about 20 carbon atoms. Also, these hydrocarbyl groups may contain heteroatoms such as oxygen, sulfur, nitrogen, silicon, and phosphorous atoms. Preferably, each X is a carboxylate group, an alkoxide group, or an aryloxide group, with each group preferably containing from 1 carbon atom, or the appropriate minimum number of carbon atoms to form these groups, up to about 20 carbon atoms.

Thus, some suitable types of organoaluminum compounds that can be utilized include, but are not limited to, trihydrocarbylaluminum, dihydrocarbylaluminum hydride, hydrocarbylaluminum dihydride, dihydrocarbylaluminum halide, hydrocarbylaluminum dihalide, dihydrocarbylaluminum carboxylate, hydrocarbylaluminum bis(carboxylate), dihydrocarbylaluminum alkoxide, hydrocarbylaluminum dialkoxide, dihydrocarbylaluminum aryloxide, hydrocarbylaluminum diaryloxide, and the like, and mixtures thereof. Trihydrocarbylaluminum compounds are generally preferred.

Some specific examples of organoaluminum compounds that can be utilized include trimethylaluminum, triethylaluminum, triisobutylaluminum, tri-n-propylaluminum, triisopropylaluminum, tri-n-hexylaluminum, tri-n-octylaluminum, tricyclohexylaluminum, triphenylaluminum, tri-p-tolylaluminum, tribenzylaluminum, diethylphenylaluminum, diethyl-p-tolylaluminum, diethylbenzylaluminum, ethyldiphenylaluminum, ethyldi-p-tolylaluminum, ethyldibenzylaluminum, diethylaluminum hydride, di-n-propylaluminum hydride, diisopropylaluminum hydride, di-n-butylaluminum hydride, diisobutylaluminum hydride, di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride, ethylaluminum dihydride, n-propylaluminum dihydride, isopropylaluminum dihydride, n-butylaluminum dihydride, isobutylaluminum dihydride, n-octylaluminum dihydride, dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, isobutylaluminum diphenoxide, and the like, and mixtures thereof.

Another class of organoaluminum compounds that can be utilized is aluminoxanes. Aluminoxanes are well known in the art and comprise oligomeric linear aluminoxanes that can be represented by the general formula:

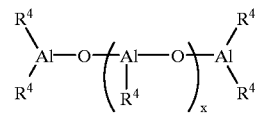

and oligomeric cyclic aluminoxanes that can be represented by the general formula:

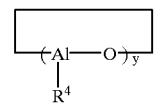

where x is an integer of 1 to about 100, preferably about 10 to about 50; y is an integer of 2 to about 100, preferably about 3 to about 20; and each $R^4$, which may be the same or different, is a mono-valent organic group. Preferably, each $R^4$ is a hydrocarbyl group such as, but not limited to, alkyl, cycloalkyl, substituted cycloalkyl, alkenyl, cycloalkenyl, substituted cycloalkenyl, aryl, allyl, substituted aryl, aralkyl, alkaryl, and alkynyl groups, with each group preferably containing from 1 carbon atom, or the appropriate minimum number of carbon atoms to form these groups, up to about 20 carbon atoms. These hydrocarbyl groups may contain heteroatoms such as oxygen, sulfur, nitrogen, silicon, and phosphorous atoms. It should be noted that the number of moles of the aluminoxane as used in this application refers to the number of moles of the aluminum atoms rather than the number of moles of the oligomeric aluminoxane molecules. This convention is commonly employed in the art.

In general, aluminoxanes can be prepared by reacting trihydrocarbylaluminum compounds with water. This reaction can be performed according to known methods, such as (1) a method in which the trihydrocarbylaluminum compound is dissolved in an organic solvent and then contacted with water, (2) a method in which the trihydrocarbylaluminum compound is reacted with water of crystallization contained in, for example, metal salts, or water absorbed in inorganic or organic compounds, and (3) a method in which the trihydrocarbylaluminum compound is added to the monomer or monomer solution that is to be oligomerized, and then water is added.

Some specific examples of suitable aluminoxane compounds include methylaluminoxane (MAO), modified methylaluminoxane (MMAO), ethylaluminoxane, butylaluminoxane, isobutylaluminoxane, and the like, and mixtures thereof. Isobutylaluminoxane is particularly useful on the grounds of its availability and its solubility in aliphatic and cycloaliphatic hydrocarbon solvents. Modified methylaluminoxane can be formed by substituting about 20–80% of the methyl groups of methylaluminoxane with $C_2$ to $C_{12}$ hydrocarbyl groups, preferably with isobutyl groups, by using techniques known to those skilled in the art.

The catalyst composition of the present invention has very high catalytic activity for oligomerizing conjugated dienes over a wide range of total catalyst concentrations and catalyst ingredient ratios. The oligomerization products having the most desirable properties, however, are obtained within a narrower range of total catalyst concentrations and catalyst ingredient ratios. Further, it is believed that the four catalyst ingredients (a), (b), (c) and (d) may interact to form an active catalyst species. Accordingly, the optimum concentration for any one catalyst ingredient is dependent upon the concentration of the other catalyst ingredients. The molar ratio of the hydrogen phosphite to the iron-containing compound (P/Fe) can be varied from about 0.5:1 to about 50:1, more preferably from about 1:1 to about 25:1, and even more preferably from about 2:1 to about 10:1. The molar ratio of the halogen-containing compound to the iron-containing compound (halogen/Fe) can be varied from about 0.5:1 to about 20:1, more preferably from about 1:1 to about 10:1, and even more preferably from about 2:1 to about 6:1. The molar ratio of the organoaluminum compound to the iron-containing compound (Al/Fe) can be varied from about 1:1 to about 100:1, more preferably from about 3:1 to about 50:1, and even more preferably from about 5:1 to about 25:1.

As discussed above, the catalyst composition of the present invention is preferably formed by combining the four catalyst ingredients (a), (b)), (c) and (d). Although an active catalyst species is believed to result from this combination, the degree of interaction or reaction between the various ingredients or components is not known with any great degree of certainty. Therefore, it should be understood that the term "catalyst composition" has been employed to encompass a simple mixture of the ingredients, a complex of the ingredients that is caused by physical or chemical forces of attraction, a chemical reaction product of the ingredients, or a combination of the foregoing.

The catalyst composition of the present invention can be formed by combining or mixing the catalyst ingredients or components by using, for example, one of the following methods:

First, the catalyst composition may be formed it situ by adding the four catalyst ingredients to a solution containing monomer and solvent, or simply bulk monomer, in either a stepwise or simultaneous manner. When adding the catalyst ingredients in a stepwise manner, the order in which the ingredients are added is not critical. Preferably, however, the iron-containing compound is added first, followed by the hydrogen phosphite, then followed by the halogen-containing compound, and finally followed by the organoaluminum compound.

Second, the four catalyst ingredients may be pre-mixed outside the oligomerization system at an appropriate temperature, which is generally from about −20° C. to about 80° C., and the resulting catalyst composition is then added to the monomer solution.

Third, the catalyst composition may be pre-formed in the presence of monomer. That is, the four catalyst ingredients are pre-mixed in the presence of a small amount of the conjugated diene monomer at an appropriate temperature, which is generally from about −20° C. to about 80° C. The amount of conjugated diene monomer that is used for the catalyst pre-forming can range from about 1 to about 500 moles per mole of the iron-containing compound, and preferably should be from about 4 to about 50 moles per mole of the iron-containing compound. The resulting catalyst composition is then added to the remainder of the monomer that is to be oligomerized.

Fourth, the catalyst composition can be formed by using a two-stage procedure. The first stage involves reacting the iron-containing compound with the organoaluminum compound in the presence of a small amount of the conjugated diene monomer at an appropriate temperature, which is generally from about −20° C. to about 80° C. In the second stage, the foregoing reaction mixture, the halogen-containing compound, and the hydrogen phosphite are then charged in either a stepwise or simultaneous manner to the remainder of the monomer that is to be oligomerized.

Fifth, an alternative two-stage procedure may be employed. An iron-ligand complex is first formed by pre-combining the iron-containing compound and the hydrogen phosphite compound. Once formed, this iron-ligand complex is then combined with the halogen-containing compound and the organoaluminum compound to form the active catalyst species. The iron-ligand complex can be formed separately or in the presence of conjugated diene monomer that is to be oligomerized. This complexation reaction can be conducted at any convenient temperature at normal pressure, but for an increased rate of reaction, it is preferred to perform this reaction at room temperature or above. The time required for the formation of the iron-ligand complex is usually within the range of about 10 minutes to about 2 hours after mixing the iron-containing compound with the hydrogen phosphite compound. The temperature and time used for the formation of the iron-ligand complex will depend upon several variables including the particular starting materials and the solvent employed. Once formed, the iron-ligand complex can be used without isolation from the complexation reaction mixture. If desired, however, the iron-ligand complex may be isolated from the complexation reaction mixture before use.

When a solution of the catalyst composition or one or more of the catalyst ingredients is prepared outside the oligomerization system as set forth in the foregoing methods, an organic solvent or carrier is preferably employed. Useful solvents include hydrocarbon solvents such as aromatic hydrocarbons, aliphatic hydrocarbons, and cycloaliphatic hydrocarbons. Non-limiting examples of aromatic hydrocarbon solvents include benzene, toluene, xylenes, ethylbenzene, diethylbenzene, mesitylene, and the like. Non-limiting examples of aliphatic hydrocarbon solvents include n-pentane, n-hexane, n-heptane, n-octane, n-nonane, n-decane, isopentane, isohexanes, isopentanes, isooctanes, 2,2-dimethylbutane, petroleum ether, kerosene, petroleum spirits, and the like. And, non-limiting examples of cycloaliphatic hydrocarbon solvents include cyclopentane, cyclohexane, methylcyclopentane, methylcyclohexane, and the like. Commercial mixtures of the above hydrocarbons may also be used. For environmental reasons, aliphatic and cycloaliphatic solvents are highly preferred. The foregoing organic solvents may serve to dissolve the catalyst ingredients or composition, or the solvent may simply serve as a carrier in which the catalyst ingredients or composition may be suspended.

As described above, the catalyst composition of the present invention exhibits very high catalytic activity for the oligomerization of conjugated dienes. Hence, the present invention further provides a process for producing conjugated diene oligomers by using the catalyst composition of this invention. Some specific examples of suitable conjugated diene monomers that can be oligomerized by means of the catalyst composition of the present invention include 1,3-butadiene, isoprene, 2,3-dimethyl-1,3-butadiene, 2-ethyl-1,3-butadiene, 1,3-pentadiene, 2-methyl-1,3-pentadiene, 3-methyl-1,3-pentadiene, 4-methyl-1,3-pentadiene, 2,4-hexadiene. The most preferred monomers are 1,3-butadiene and isoprene. Mixtures of the above conjugated diene monomers may also be utilized in co-oligomerization. As described above, there are available a variety of methods for bringing the ingredients of the catalyst composition into contact with conjugated diene monomers.

The production of conjugated diene oligomers according to this invention is accomplished by oligomerizing conjugated diene monomers in the presence of a catalytically effective amount of the foregoing catalyst composition. To understand what is meant by a catalytically effective amount, it should be understood that the total catalyst concentration to be employed in the oligomerization mass depends on the interplay of various factors such as the purity of the ingredients, the oligomerization rate and conversion desired, the oligomerization temperature, and many other factors. Accordingly, specific total catalyst concentrations cannot be definitively set forth except to say that catalytically effective amounts of the respective catalyst ingredients should be used. Generally, the amount of the iron-containing compound used can be varied from about 0.01 to about 2 mmol per 100 g of the conjugated diene monomer, with a more preferred range being from about 0.02 to about 1.0 mmol per 100 g of the conjugated diene monomer, and a most preferred range being from about 0.05 to about 0.5 mmol per 100 g of the conjugated diene monomer.

The oligomerization of conjugated dienes according to this invention is preferably carried out in an organic solvent as the diluent. That is, an amount of the organic solvent in addition to the organic solvent that may be used in preparing the catalyst composition is added to the oligomerization system. The additional organic solvent may be either the same as or different from the organic solvent contained in the catalyst solutions. It is normally desirable to select an organic solvent that is inert with respect to the catalyst composition employed to catalyze the oligomerization reaction. Suitable types of organic solvents that can be utilized as the diluent include, but are not limited to, aliphatic, cycloaliphatic, and aromatic hydrocarbons. Some representative examples of suitable aliphatic solvents include n-pentane, n-hexane, n-heptane, n-octane, n-nonane, n-decane, isopentane, isohexanes, isopentanes, isooctanes, 2,2-dimethylbutane, petroleum ether, kerosene, petroleum spirits, and the like. Some representative examples of suitable cycloaliphatic solvents include cyclopentane, cyclohexane, methylcyclopentane, methylcyclohexane, and the like. Some representative examples of suitable aromatic solvents include benzene, toluene, xylenes, ethylbenzene, diethylbenzene, mesitylene, and the like. Commercial mixtures of the above hydrocarbons may also be used. For environmental reasons, aliphatic and cycloaliphatic solvents are highly preferred.

The concentration of the conjugated diene monomer to be oligomerized is not limited to a special range. Generally, however, it is preferred that the concentration of the conjugated diene in the oligomerization medium at the beginning of the oligomerization be in a range of from about 3% to about 80% by weight, more preferably from about 5% to about 50% by weight, and even more preferably from about 10% to about 30% by weight.

The oligomerization of conjugated dienes according to this invention may also be carried out by means of bulk oligomerization, which refers to a reaction environment where no solvents are employed. Bulk oligomerization can be conducted either in a condensed liquid phase or in a gas phase.

The oligomerization of conjugated dienes according to this invention may be carried out as a batch process, continuous process, or even semi-continuous process. In the semi-continuous process, conjugated diene monomer is intermittently charged as needed to replace that monomer already oligomerized. In any case, the oligomerization is desirably conducted under anaerobic conditions by using an inert protective gas such as nitrogen, argon, or helium, with moderate to vigorous agitation. The oligomerization temperature employed in the practice of this invention may vary widely from a low temperature, such as $-10°$ C. or below, to a high temperature such as $100°$ C. or above, with a preferred temperature range being from about $20°$ C. to about $90°$ C. In general, elevated temperatures are undesirable due to thermal polymerization of the oligomers. The heat of oligomerization may be removed by external cooling, cooling by evaporation of the conjugated diene monomer or the solvent, or a combination of the two methods. Although the pressure employed in the practice of this invention also may vary widely, a preferred pressure range is from about 1 atmosphere to about 10 atmospheres.

The reaction time for the oligomerization process of this invention can vary widely but will generally be from a few minutes, e.g., 5 minutes, to a few hours, e.g., 4 hours, depending upon factors such as the type of conjugated diene, the temperature, the catalyst concentration, the catalyst ingredient ratio, and the conversion desired. In general, due to the very high catalytic activity of the catalyst composition of this invention, the reaction time is quite short even with the use of very low catalyst levels. Therefore, high conversion and high productivity in terms of pounds of product per pound of catalyst per hour are realized. Furthermore, since the catalyst composition of this invention is highly active even at low temperatures, the oligomerization of conjugated dienes may be carried out under very mild temperature conditions, thereby minimizing the formation of undesirable by-products.

Once a desired conversion is achieved, the oligomerization reaction can be stopped by the addition of a terminator that inactivates the catalyst. Typically, the terminator employed is a protic compound, which includes, but is not limited to, an alcohol, a carboxylic acid, an inorganic acid, water, or a combination thereof.

A stabilizer such as 2,6-di-tert-butyl-4-methylphenol may be added along with, before, or after addition of the terminator. The amount of the stabilizer employed is usually in the range of 0.01% to 0.1% by weight of the oligomerization product. When the oligomerization reaction has been stopped, the products can be recovered from the reaction mixture by conventional techniques such as fractional distillation and preparative chromatography, which are well known to those skilled in the art.

In order to demonstrate the practice of the present invention, the following examples have been prepared and tested. The examples should not, however, be viewed as limiting the scope of the invention. The claims will serve to define the invention.

EXAMPLES

Example 1

An oven-dried 1-liter glass bottle was capped with a self-sealing rubber liner and a perforated metal cap, and then purged with a stream of dry nitrogen. The bottle was charged with 68 g of hexanes and 182 g of a 1,3-butadiene/hexanes blend containing 27.5% by weight of 1,3-butadiene. The following catalyst ingredients were added to the bottle in the following order: (1) 0.050 mmol of iron(III) 2-ethylhexanoate, (2) 0.20 mmol of bis(2-ethylhexyl) hydrogen phosphite, (3) 0.15 mmol of diisobutylaluminum chloride, and (4) 0.70 mmol of triisobutylaluminum. The oligomerization of 1,3-butadiene started immediately as indicated by the rise in temperature of the reaction mixture. The bottle was immediately placed in a water bath maintained at room temperature. After 2 hours, the oligomerization was terminated by addition of 1 mL of isopropanol. The analysis of the resulting oligomerization mixture by using gas chromatography/mass spectrometry (GC/MS) indicated that 100% of the 1,3-butadiene monomer used was converted, resulting in the following product distribution: 5-methyl-1,3,6-heptatriene (87.9%), 1,3,6-octariene (11.9%), and 4-vinyl-1-cyclohexene (0.2%). These results show that at mild temperature conditions, 1,3-butadiene can be converted quantitatively to mostly the two acyclic dimers with a selectivity of 99.8% by utilizing the catalyst composition of the present invention.

Examples 2–5

In Examples 2–5, the procedure in Example 1 was repeated except that the catalyst ingredient ratio was varied as shown in Table I. The monomer charge, the amounts of the catalyst ingredients, and the oligomerization product distributions are summarized in Table I.

Examples 6–10

In Examples 6–10, the procedure described in Example 1 was repeated except that a cyclic hydrogen phosphite compound, i.e., 2-oxo-(2H)-5-butyl-5-ethyl-1,3,2-dioxaphosphorinane, was substituted for bis(2-ethylhexyl) hydrogen phosphite, and the catalyst ingredient ratio was varied as shown in Table II. The monomer charge, the amounts of the catalyst ingredients, and the oligomerization product distributions are summarized in Table II.

TABLE II

| Example No. | 6 | 7 | 8 | 9 | 10 |
|---|---|---|---|---|---|
| Hexane (g) | 68 | 68 | 68 | 68 | 68 |
| 27.5% 1,3-Bd/hexanes (g) | 182 | 182 | 182 | 182 | 182 |
| Fe(2-EHA)$_3$ (mmol) | 0.050 | 0.050 | 0.050 | 0.050 | 0.050 |
| Cyclic hydrogen phosphite* (mmol) | 0.20 | 0.20 | 0.20 | 0.20 | 0.20 |
| i-Bu$_2$AlCl (mmol) | 0.15 | 0.15 | 0.15 | 0.15 | 0.15 |
| i-Bu$_3$Al (mmol) | 0.65 | 0.70 | 0.75 | 0.80 | 0.85 |
| Fe/P/Cl/Al molar ratio | 1:4:3:13 | 1:4:3:14 | 1:4:3:15 | 1:4:3:16 | 1:4:3:17 |
| Conversion (%) after 2 hr | 99.1 | 99.1 | 99.1 | 100 | 100 |
| Oligomerization product distribution: | | | | | |
| 5-Methyl-1,3,6-heptatriene (%) | 72.0 | 71.8 | 72.2 | 72.3 | 72.2 |
| 1,3,6-Octatriene (%) | 27.8 | 28.0 | 27.6 | 27.5 | 27.6 |
| 4-Vinyl-1-cyclohexene (%) | 0.2 | 0.2 | 0.2 | 0.2 | 0.2 |

*The cyclic hydrogen phosphite used was 2-oxo-(2H)-5-butyl-5-ethyl-1,3,2-dioxaphosphorinane.

Various modifications and alterations that do not depart from the scope and spirit of this invention will become apparent to those skilled in the art. This invention is not to be duly limited to the illustrative embodiments set forth herein.

What is claimed is:

1. A catalyst composition that is the combination of or the reaction product of ingredients comprising:
   (a) an iron-containing compound;
   (b) a hydrogen phosphite;
   (c) a halogen-containing compound; and
   (d) an organoaluminum compound.

2. The catalyst composition of claim 1, where the iron-containing compound is an iron carboxylate, iron carbamate, iron dithiocarbamate, iron xanthate, iron β-diketonate, iron alkoxide, iron aryloxide, iron halide, iron pseudo-halide, iron oxyhalide, organoiron compound, or a mixtures thereof.

TABLE I

| Example No. | 1 | 2 | 3 | 4 | 5 |
|---|---|---|---|---|---|
| Hexanes (g) | 68 | 68 | 68 | 68 | 68 |
| 27.5% 1,3-Bd/hexanes (g) | 182 | 182 | 182 | 182 | 182 |
| Fe(2-EHA)$_3$ (mmol) | 0.050 | 0.050 | 0.050 | 0.050 | 0.050 |
| HP(O)(OCH$_2$CH(Et)(CH$_2$)$_3$CH$_3$)$_2$ (mmol) | 0.20 | 0.20 | 0.20 | 0.20 | 0.20 |
| i-BU$_2$AlCl (mmol) | 0.15 | 0.15 | 0.15 | 0.15 | 0.15 |
| i-Bu$_3$Al (mmol) | 0.70 | 0.75 | 0.80 | 0.85 | 0.90 |
| Fe/P/Cl/Al molar ratio | 1:4:3:14 | 1:4:3:15 | 1:4:3:16 | 1:4:3:17 | 1:4:3:18 |
| Conversion (%) after 2 hr | 100 | 100 | 100 | 100 | 100 |
| Oligomerization product distribution: | | | | | |
| 5-Methyl-1,3,6-heptatriene (%) | 87.9 | 87.9 | 88.1 | 88.3 | 88.2 |
| 1,3,6-Octatriene (%) | 11.9 | 11.9 | 11.7 | 11.5 | 11.6 |
| 4-Vinyl-1-cyclohexene (%) | 0.2 | 0.2 | 0.2 | 0.2 | 0.2 |

3. The catalyst composition of claim 1, where the hydrogen phosphite is an acyclic hydrogen phosphite defined by the following keto-enol tautomeric structures:

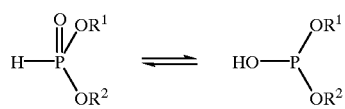

or a cyclic hydrogen phosphite defined by the following keto-enol tautomeric structures:

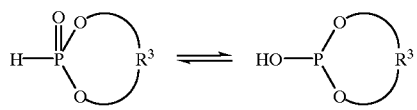

or a mixture thereof, where $R^1$ and $R^2$, which may be the same or different, are mono-valent organic groups, and where $R^3$ is a divalent organic group.

4. The catalyst composition of claim 3, where $R^1$ and $R^2$ are alkyl, cycloalkyl, substituted cycloalkyl, alkenyl, cycloalkenyl, substituted cycloalkenyl, aryl, allyl, substituted aryl, aralkyl, alkaryl, or alkynyl groups, with each group containing up to about 20 carbon atoms, and where $R^3$ is an alkylene, cycloalkylene, substituted alkylene, substituted cycloalkylene, alkenylene, cycloalkenylene, substituted alkenylene, substituted cycloalkenylene, arylene, or substituted arylene group, with each group containing up to about 20 carbon atoms.

5. The catalyst composition of claim 1, where the halogen-containing compound is an elemental halogen, mixed halogen, hydrogen halide, organic halide, inorganic halide, metallic halide, organometallic halide, or a mixture thereof.

6. The catalyst composition of claim 1, where the organoaluminum compound is defined by the formula $AlR_nX_{3-n}$, where each R, which may be the same or different, is a mono-valent organic group, where each X, which may be the same or different, is a hydrogen atom, a halogen atom, a carboxylate group, an alkoxide group, or an aryloxide group, and where n is an integer including 1, 2 or 3.

7. The catalyst composition of claim 6, where each R is an alkyl, cycloalkyl, substituted cycloalkyl, alkenyl, cycloalkenyl, substituted cycloalkenyl, aryl, allyl, substituted aryl, aralkyl, alkaryl, or alkynyl group, with each group containing up to about 20 carbon atoms, and where each X is a carboxylate group, an alkoxide group, or an aryloxide group, with each group containing up to about 20 carbon atoms.

8. The catalyst composition of claim 1, where the organoaluminum compound is trihydrocarbylaluminum, dihydrocarbylaluminum hydride, hydrocarbylaluminum dihydride, dihydrocarbylaluminum halide, hydrocarbylaluminum dihalide, dihydrocarbylaluminum carboxylate, hydrocarbylaluminum bis(carboxylate), dihydrocarbylaluminum alkoxide, hydrocarbylaluminum dialkoxide, dihydrocarbylaluminum aryloxide, hydrocarbylaluminum diaryloxide, or a mixture thereof.

9. The catalyst composition of claim 1, where the organoaluminum compound is defined by one of the following formulas:

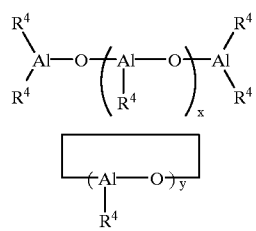

where x is an integer of 1 to about 100, y is an integer of 2 to about 100, and each $R^4$, which may be the same or different, is a mono-valent organic group.

10. The catalyst composition of claim 9, where each $R^4$ is an alkyl, cycloalkyl, substituted cycloalkyl, alkenyl, cycloalkenyl, substituted cycloalkenyl, aryl, allyl, substituted aryl, aralkyl, alkaryl, or alkynyl group, with each group containing up to about 20 carbon atoms.

11. The catalyst composition of claim 1, where the molar ratio of the hydrogen phosphite to the iron-containing compound is from about 0.5:1 to about 50:1, the molar ratio of the halogen-containing compound to the iron-containing compound is from about 0.5:1 to about 20:1, and the molar ratio of the organoaluminum compound to the iron-containing compound is from about 1:1 to about 100:1.

12. The catalyst composition of claim 11, where the molar ratio of the hydrogen phosphite to the iron-containing compound is from about 1:1 to about 25:1, the molar ratio of the halogen-containing compound to the iron-containing compound is from about 1:1 to about 10:1, and the molar ratio of the organoaluminum compound to the iron-containing compound is from about 3:1 to about 50:1.

13. A catalyst composition formed by a process comprising the step of combining:
   (a) an iron-containing compound;
   (b) a hydrogen phosphite;
   (c) a halogen-containing compound; and
   (d) an organoaluminum compound.

14. A process for forming conjugated diene oligomers comprising the step of:
   oligomerizing conjugated diene monomers in the presence of a catalytically effective amount of a catalyst composition formed by combining:
   (a) an iron-containing compound;
   (b) a hydrogen phosphite;
   (c) a halogen-containing compound; and
   (d) an organoaluminum compound.

15. The process of claim 14, where the hydrogen phosphite is an acyclic hydrogen phosphite defined by the following keto-enol tautomeric structures:

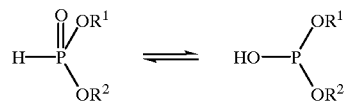

or a cyclic hydrogen phosphite defined by the following keto-enol tautomeric structures:

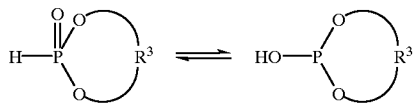

or a mixture thereof, where $R^1$ and $R^2$, which may be the same or different, are mono-valent organic groups, and where $R^3$ is a divalent organic group.

16. The process of claim 15, where $R^1$ and $R^2$ are alkyl, cycloalkyl, substituted cycloalkyl, alkenyl, cycloalkenyl, substituted cycloalkenyl, aryl, allyl, substituted aryl, aralkyl, alkaryl, or alkynyl groups, with each group containing up to about 20 carbon atoms, and where $R^3$ is an alkylene, cycloalkylene, substituted alkylene, substituted cycloalkylene, alkenylene, cycloalkenylene, substituted alkenylene, substituted cycloalkenylene, arylene, or substituted arylene group, with each group containing up to about 20 carbon atoms.

17. The process of claim 14, where the halogen-containing compound is an elemental halogen, mixed halogen, hydrogen halide, organic halide, inorganic halide, metallic halide, organometallic halide, or a mixture thereof.

18. The process of claim 14, where the organoaluminum compound is defined by the formula $AlR_nX_{3-n}$, where each R, which may be the same or different, is a mono-valent organic group, where each X, which may be the same or different, is a hydrogen atom, a halogen atom, a carboxylate group, an alkoxide group, or an aryloxide group, and where n is an integer including 1, 2 or 3.

19. The process of claim 14, where the organoaluminum compound is selected from aluminoxanes defined by one of the following formulas:

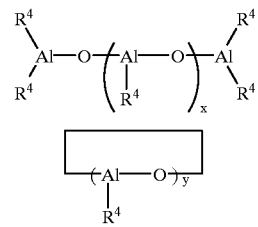

where x is an integer of 1 to about 100, y is an integer of 2 to about 100, and each $R^4$, which may be the same or different, is a mono-valent organic group.

20. The catalyst composition of claim 1 wherein the iron atom of the iron-containing compound has an oxidation state of 0, +2, or +4.

21. The catalyst composition of claim 1 wherein the halogen-containing compound is selected from the group consisting of elemental halogens, mixed halogens, hydrogen halides, organic halides, inorganic halides, and organometallic halides.

22. The catalyst composition of claim 21 wherein the iron-containing compound is selected from the group consisting of iron carboxylates, iron carbamates, iron dithiocarbamates, iron xanthates, iron β-diketonates, iron alkoxides or aryloxides, iron oxyhalides, and organoiron compounds.

* * * * *